United States Patent [19]

Farrar et al.

[11] Patent Number: 5,667,773
[45] Date of Patent: Sep. 16, 1997

[54] FILM-FORMING COMPOSITIONS OF ANTIHYPERALGESIC OPIATES AND METHOD OF TREATING HYPERALGESIC CONDITIONS THEREWITH

[75] Inventors: John J. Farrar, Chester Springs; Alan L. Maycock, Malvern; Virendra Kumar, Paoli; Imre (Jim) Balogh, Perkasie, all of Pa.

[73] Assignee: Adolor Corporation, Malvern, Pa.

[21] Appl. No.: 614,027

[22] Filed: Mar. 12, 1996

[51] Int. Cl.$^6$ .................. A61K 31/00; A61K 9/08; A61K 7/40
[52] U.S. Cl. .................. 424/78.05; 424/78.06; 424/78.07; 514/772.3; 514/777; 514/817
[58] Field of Search .................. 424/488, 78.05, 424/78.06, 78.07

[56] References Cited

U.S. PATENT DOCUMENTS

| | | |
|---|---|---|
| 3,714,159 | 1/1973 | Janssen et al. . |
| 3,884,916 | 5/1975 | Janssen et al. . |
| 3,996,214 | 12/1976 | Dajani et al. . |
| 4,012,393 | 3/1977 | Markos et al. . |
| 4,013,668 | 3/1977 | Adelstein et al. . |
| 4,025,652 | 5/1977 | Diamond et al. . |
| 4,060,635 | 11/1977 | Diamond et al. . |
| 4,115,564 | 9/1978 | Diamond et al. . |
| 4,203,920 | 5/1980 | Diamond et al. . |
| 4,326,074 | 4/1982 | Diamond et al. . |
| 4,326,075 | 4/1982 | Diamond et al. . |
| 4,533,739 | 8/1985 | Pitzele et al. . |
| 4,623,539 | 11/1986 | Tunc . |
| 4,946,870 | 8/1990 | Kurazumi et al. ............ 424/439 |
| 5,236,947 | 8/1993 | Calvet et al. . |
| 5,242,944 | 9/1993 | Park et al. . |
| 5,258,436 | 11/1993 | Wheatley et al. ............ 524/388 |
| 5,348,744 | 9/1994 | Partain, III ............ 514/777 |

*Primary Examiner*—Peter F. Kulkosky
*Attorney, Agent, or Firm*—Imre Balogh

[57] ABSTRACT

Topical anti-hyperalgesic film-forming compositions and methods of using compositions for the treatment of peripheral hyperalgesia comprising:

a) a compound of the formula

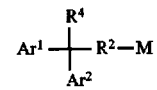

wherein M is

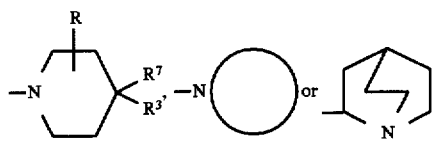

wherein:
R, $R^2$, $R^3$, $R^4$, $R^7$, $Ar^1$ and $Ar^2$ are as defined in the specification;

b) a film-forming polymeric material containing the hyperalgesic compound; and c) an aqueous pharmaceutically acceptable carrier.

5 Claims, No Drawings

FILM-FORMING COMPOSITIONS OF ANTIHYPERALGESIC OPIATES AND METHOD OF TREATING HYPERALGESIC CONDITIONS THEREWITH

BACKGROUND OF THE INVENTION

1. Field of the Invention

This invention relates to film-forming compositions of anti-hyperalgesic opiates having substantially no effects on the central nervous system and method of topically treating hyperalgesic conditions.

2. Reported Developments

Pain is the effect of noxious stimuli on nerve endings of a subject which results in the transmission of impulses to the cerebrum. This sensation informs the subject of actual or impending tissue damage and elicits a defensive response. The degree of response substantially correlates with the degree of noxious stimuli in order to speedily avoid further tissue damage and to re-establish normal pre-injury conditions in the subject. The sensation of pain, however, does not end with the stoppage of the noxious stimuli but continues to persist during the inflammation stage of the injury. In turn, the continuation of pain perception causes discomfort to, and deleteriously affects the well-being of, the subject. It is, therefore, important to reduce and/or eliminate pain perception of a subject subsequent to injuries.

The reduction/elimination of pain perception can be affected by the central nervous system (hereinafter sometimes referred to as CNS)-mediated analgesia which leads to an overall inhibition of the pain transmission. CNS-mediated analgesia can be effected by systemically administered opiates which, by interaction with specific receptors in the brain and spinal cord, are able to block pain transmission. Systemic opiates, such as morphine, which have been used for many years to control post injury pain, have side effects because their actions within the brain include sedation, depression of respiration, constipation, nausea and development of addiction and dependence. When peripherally applied, opiates have a short duration of action and still possess the undesirable side effects.

Certain opiates, such as loperamide [i.e., 4-(p-chlorophenyl)-4-hydroxy-N-N-dimethyl-α,α-diphenyl-1-piperidinebutyramide hydrochloride] and its analogs were reported to be devoid of CNS effects, which is believed to be due to the failure of the opiates to cross the blood brain barrier. Loperamide HCl has been used for a long time in antidiarrheal formulations and has been completely free of the undesirable CNS effects. It would be desirable to use such opiates to inhibit/eliminate post-injury pain without concomitant CNS effects.

It would also be desirable to provide compositions and method for conveniently delivering the compounds to the site of injury.

Therefore, it is an object of the present invention to provide a safe and effective topical composition for inhibiting/eliminating the sensation of pain.

It is another object of the present invention to provide a convenient method of delivering such compositions to the site of injury.

These and other objects are accomplished by delivering a composition to the site of injury, said composition comprising a compound having anti-hyperalgesic activity incorporated in a film-forming composition.

SUMMARY OF THE INVENTION

In accordance with the present invention a topical antihyperalgesic composition is provided comprising:

(a) from about 1.0 to about 65% w/w of an antihyperalgesic compound incorporated in a film-forming polymeric material;

(b) said film-forming polymeric material being present in said composition of from about 1 to about 76% w/w and is capable of forming an essentially continuous film in the pH environment of from about 5.5 to about 8.5, said polymeric material having atoms containing polarizable electrons thereon, said atoms being selected from the group consisting of oxygen, nitrogen, sulfur in combination with a divalent cation, said divalent cation is selected from the group consisting of $Ca^{++}$, $Mg^{++}$, $Zn^{++}$ and $Ba^{++}$ wherein the ratio of said atoms containing polarizable electrons thereon to said divalent cations is in the range of from about 7.7 to about 1; and (c) of from about 23 to about 34% w/w of an aqueous pharmaceutically acceptable carrier.

In another aspect the present invention provides a method for the inhibition of post-injury pain associated with local inflammatory conditions including inflammation following infection, blisters, boils, acute skin injuries, abrasions, burns, cuts, contusions, surgical incisions, irritations from various sources, poison ivy, allergic rashes, dermatitis, stings and bites and inflammation of joints by depositing the topical composition onto the site of the condition where the sensation of pain occurs.

DETAILED DESCRIPTION OF THE INVENTION

The Anti-Hyperalgesic Compounds

The compounds intended for use in the compositions and methods herein possess peripheral anti-hyperalgesic and substantially no CNS activities because they do not cross the blood brain barrier. The failure to cross the blood brain barrier precludes the occurrence of the CNS systemic side effects, so that there is no potential for abuse. The compounds intended for use in the methods and compositions provided herein include any compound that by virtue of its interaction, either directly or indirectly, with peripheral opioid receptors ameliorates the peripheral hyperalgesic state, but does not exhibit systemic CNS-mediated analgesic activity or CNS side effects, including heaviness of the limbs, flush or pale complexion, clogged nasal and sinus passages, dizziness, depression, respiratory depression, sedation and constipation. These compounds include antidiarrheals that act as antidiarrheals via interaction, with $\mu$, $\delta$, or $\kappa$ receptors, and opiate agonists, such as metkephamide and related enkephalin analogs. The compounds of the present invention, the description of which follows, have been reported in prior art patents all of which are incorporated herein by reference:

(a) Loperamide, its analogs, and its related compounds, metabolites and prodrugs thereof reported in U.S. Pat. Nos.

| | |
|---|---|
| 3,714,159 | 4,125,531 |
| 3,884,916 | 4,194,045 |
| 3,996,214 | 4,203,920 |
| 4,012,393 | 4,277,605 |
| 4,013,668 | 4,326,074 |
| 4,025,652 | 4,326,075 |
| 4,060,635 | 4,533,739 |
| 4,066,654 | 4,824,853 |
| 4,069,223 | 4,990,521 |
| 4,072,686 | 5,236,947 |
| 4,115,564 | 5,242,944 |
| 4,116,963 | |

Such compounds include compounds of Formula I; its N-oxide or a pharmaceutically acceptable salt or acid:

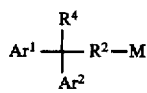  I wherein M is

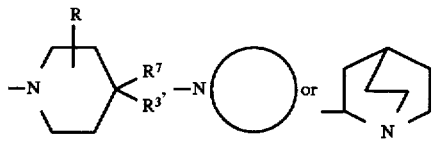

wherein:

is an azabicycloalkyl containing from 6 to 9 carbon atoms with at least 5 atoms in each ring and is unsubstituted or substituted with $OR^{18}$ in which $R^{18}$ is hydrogen or lower alkanoyl containing 2 to 7 carbons and $OR^{18}$ is at the 5 position in 5-membered rings or the 5 or 6 position in 6-membered rings and is attached in the endo or exo configuration;

$Ar^1$ and $Ar^2$ are either (i) or (ii) as follows:
(i) each is independently selected from aryl and heteroaryl groups containing from 5 to 7 members in the ring, each is unsubstituted or substituted with one or more substituents selected from halo, haloalkyl, hydroxy, alkyl, alkyloxy, aminosulfonyl, alkylcarbonyl, nitro, haloalkyl, trifluoromethyl, amino, aminocarbonyl, phenylcarbonyl or thienyl, where the alkyl groups are straight or branched chains lower alkyl containing from 1 to 6 carbon atoms; or
(ii) $Ar^1$ and $Ar^2$ are each independently phenyl or pyridyl groups and with the carbon to which they are commonly linked form a fused ring so that the compounds of formula (I) have the structure:

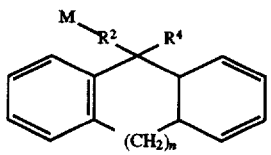

wherein n is 0 to 3;

$R^2$ is either alkyl in which the alkyl group is a straight or branched chain having 1 to 12 carbon atoms, or is alkylene having 1 to 6 carbon atoms with one or two double bonds;

$R^3$ is $Ar^3$, —Y—$Ar^3$, where Y is alkylene or alkyl having 1 to 3 carbon atoms, or is

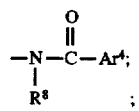

$R^8$ is hydrogen or alkyl that is a straight or branched chain containing from 1 to 6 carbon atoms;

$Ar^3$ is aryl or heteroaryl containing from 5 to 7 members in the ring, which is unsubstituted or substituted with one or more substituents of halo, halo lower alkyl or lower alkyl;

$Ar^4$ is either:
(i) is a heterocycle containing one to three fused rings or which is unsubstituted or substituted with one or more substituents selected from halo, halo lower alkyl or lower alkyl, or
(ii) $Ar^4$ is a radical of formula:

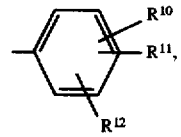

in which $R^{10}$, $R^{11}$ and $R^{12}$ are each independently selected from hydrogen, alkyl, alkyloxy, alkoxyalkyl, halo, haloalkyl, hydroxy, cyano, nitro, amino, alkylamino, di(alkyl)amino, aminocarbonyl, arylcarbonylamino, alkylcarbonylamino, alkylcarbonyl, alkylcarbonyloxy, aminosulfonyl, alkylsulfinyl, alkylsulfonyl, alkylthio, mercapto, $C_3$–$C_6$ alkenyloxy, arylalkyloxy, aryloxy or alkyl, in which each group is unsubstituted or substituted with one or more halo atoms, halo alkyl or alkyl, and the alkyl groups are straight or branched chains that are lower alkyl;

R is hydrogen, alkyl, halo, haloalkyl or $OR^9$;

$R^9$ is selected from alkyl, arylalkyl, alkylcarbonyl, aminoalkyl, alkylaminoalkyl or dialkylaminoalkyl, in which the alkyl groups are straight or branched chains containing 1 to 12 carbon atoms;

$R^4$ is selected from among:
(i) 5- to 7-membered aryl groups, which are unsubstituted or substituted with lower alkyl, halo lower alkyl or halo, or
(ii) heterocyclic rings, containing one to three heteroatoms, that are unsubstituted or substituted with halo, halo lower alkyl or lower alkyl, or
(iii) alkyl containing from 1 to 8 carbon atoms, alkenyl containing 3 to 6 carbon atoms, cycloalkyl containing from 3 to 6 carbon atoms, cycloalkyl alkyl in which the first alkyl contains 3 to 6 carbons and the second containing 1 to 3 carbons, or cycloalkenyl containing 4 to 7 carbons, or

where $R^5$ and $R^6$ are either:
(i) independently selected from hydrogen, alkyl, which is a straight or branched chain containing 1 to 12 carbon atoms, alkenyl, which is straight or branched chain, containing 1 to 12 carbon atoms and one or two double bonds, or aryl, which contains 5 to 7 carbon atoms, or
(ii) $R^5$ and $R^6$ are selected from carbon chains, heteroatoms, and carbon chains containing one or more heteroatoms, so that with the nitrogen atoms to which each is attached they form a 3- to 7-membered heterocyclic ring containing one to three heteroatoms that is unsubstituted or substituted with halo, halo lower alkyl or lower alkyl; and $R^7$ is selected from among:
H;
OH;

—$R^{14}OR^{13}$ in which $R^{13}$ is hydrogen or lower alkyl, alkanoyl containing 2 to 5 carbon atoms, and $R^{14}$ is lower alkenyl or lower alkyl;

—$CH_2NR^{15}R^{16}$ in which $R^{15}$ is hydrogen, lower alkyl or lower alkanoyl and $R^{16}$ is hydrogen or lower alkyl;

$OR^{15}$;

$R^{22}OR^{13}$, in which $R^{22}$ is lower alkyl;

—$C(O)OR^{17}$ in which $R^{17}$ is hydrogen, alkyl containing form 1 to 7 carbons or alkenyl having 3–7 carbon atoms, aryl or heteroaryl; or an alkali metal or alkaline earth metal salt.

The nomenclatures are to be understood to have the meaning generally understood by those skilled in the art as defined herein:

"Halogen" or "halide" or "halo" refers to F, Cl, Br or I, and also pseudohalides. In preferred embodiments halo refers to F, Cl, Br and I.

Pseudohalides are radicals that behave substantially similar to halides. Such radicals can be used in the same manner and treated in the same manner as halides (X, in which X is a halogen, such as Cl or Br). Pseudohalides include, but are not limited to cyanide, cyanate, thiocyanate, selenocyanate, azide and trifluoromethyl. As used herein, carbon chains and carbon chains with heteroatoms may be straight or branched or, if they contain 3 or more members, may be cyclic.

Alkyl, alkenyl and alkynyl carbon chains, if not specified contain from 1 to 20 carbons, preferably 1 to 12 carbons and are straight or branched.

Lower alkyl, lower alkenyl, and lower alkynyl refer to carbon chains having one to about 6 carbons. In preferred embodiments of the compounds provided herein that includes alkyl, alkenyl, or alkynyl portions include lower alkyl, lower alkenyl and lower alkynyl portions. Preferred among lower carbon chains are those having 1–3 carbons.

Aryl refers to cyclic groups containing from 3 to 15 or 16 carbon atoms, preferably from 5 to 10, more preferably 5 to 7 carbons. Aryl groups include, but are not limited to, groups such as phenyl, substituted phenyl, naphthyl, substituted naphthyl, in which the substituent is lower alkyl, halo, halo lower alkyl, or lower alkoxy. Preferred aryl groups are lower aryl groups that contain less than 7 carbons in the ring structure.

Cycloalkyl refers to saturated cyclic carbon chains; cycloalkyenyl and cycloalkynyl refer to cyclic carbon chains that include at least one unsaturated triple bond. The cyclic portions of the carbon chains may include one ring or two or more fused rings.

Carbocyclic group is a ring containing at least three carbons; a heterocyclic group is a ring containing at least one carbon and one or more heteroatoms, preferably selected from among O, S and N, more preferably N and O. A heteroaryl group is an unsaturated ring structure containing 1 or more, preferably 1 to 3 heteroatoms in the ring. The rings may be single or two or more fused rings. Heteroaryl is used interchangeably with heterocycle.

Heterocycle refers to ring structures that include at least one carbon atom and one or more atoms, such as N, S, and O.

Alkyl refers to non-aromatic carbon chains that contain one or more carbons; the chains may be straight or branched or include cyclic portions or be cyclic.

Alicyclic refers to aryl groups that are cyclic.

Haloalkyl refers to an alkyl radical, preferably lower alkyl, in which one or more of the hydrogen atoms are replaced by halogen including, but not limited to, chloromethyl, trifluoromethyl, 1-chloro-2-fluoroethyl and other such groups. Halo lower alkyl refers to lower alkyl substituted with one or more halo substituents, and is preferably trichloromethyl or trifluoromethyl.

Haloalkoxy refers to RO— in which R is a haloalkyl group.

Aminocarbonyl refers to —$C(O)NH_2$.

Alkylaminocarbonyl refers to —$C(O)NHR$ in which R is hydrogen, alkyl, preferably lower alkyl or aryl, preferably lower aryl.

Dialkylaminocarbonyl refers to —$C(O)NR'R$ in which R' and R are independently selected from alkyl or aryl, preferably lower alkyl or lower aryl; carboxamide: refers to groups of formula NR'COR.

Alkoxycarbonyl as used herein refers to —$C(O)OR$ in which R is alkyl, preferably lower alkyl or aryl, preferably lower aryl.

Alkoxy and thioalkoxy refer to RO— and RS—, in which R is alkyl, preferably lower alkyl or aryl, preferably lower aryl.

When a particular group, such as phenyl or pyridyl is specified, this means that the group is unsubstituted or is substituted.

The compounds can be made as described in the above-cited and herein incorporated patents of which the following are preferred.

2-[4-(4-hydroxy-4-phenylpiperidino)-2,2-diphenylbutyryl]-piperidine;

4-{4-[4-hydroxy-4-(3-trifluoromethylphenyl)piperidino]-2,2-diphenylbutyryl}morpholine;

1-{4-[4-hydroxy-4-(3-trifluoromethylphenyl)-piperidino]-2,2-diphenylbutyl}piperidine;

4-(p-chlorophenyl)-4-hydroxy-N-N-,y-trimethyl-α,α-diphenylpiperidine-1-butyramide;

4-(p-chlorophenyl)-4-hydroxy-N-N-dimethyl-α,α-diphenylpiperidine-1-butyramide[loperamide];

4-(3,4-dichlorophenyl)-N-N-diethyl-4-hydroxy-α,α-diphenylpiperidine-1-butyramide;

4-(3,4-dichlorophenyl)-4-hydroxy-N-N-dimethyl-α,α-diphenylpiperidine-1-butyramide;

4-(4-chloro-3-trifluoromethylphenyl)-4-hydroxy-N-N-dimethyl-α,α-diphenylpiperidine-1-butyramide;

4-(p-fluorophenyl)-4-hydroxy-N-N-,y-trimethyl-α,α-diphenylpiperidine-1-butyramide;

4-(p-bromophenyl)-4-hydroxy-N-N-dimethyl-α,α-diphenylpiperidine-1-butyramide;

1-{4-[4-(3,4-dichlorophenyl)-4-hydroxypiperidino]-2,2-diphenylbutyryl}pyrrolidine;

4-(p-chlorophenyl)-N-ethyl-4-hydroxy-N-methyl-α,α-diphenylpiperidine-1-butyramide;

5-[1,1-diphenyl-3-(exo-5-hydroxy-2-azabicyclo[2,2-2]oct-2-yl)-propyl]-2-methyl-1,3,4-oxadiazole;

5-[1,1-diphenyl-3-(exo-5-acetoxy-2-azabicyclo[2.2-2]oct-2-yl)-propyl]-2-methyl-1,3,4-oxadiazole;

5-[1,1-diphenyl-3-(endo-5-acetoxy-2-azabicyclo[2.2-2]oct-2-yl)-propyl]-

5-[1,1-diphenyl-3-(endo-5-hydroxy-2-azabicyclo[2.2-2]oct-2-yl)-propyl]-2-methyl-1,3,4-oxadiazole;

5-[1,1-diphenyl-3-(endo-6-acetoxy-2-azabicyclo[2.2-2]oct-2-yl)-propyl]-2-methyl-1,3,4-oxadiazole;

5-[1,1-diphenyl-3-(endo-6-hydroxy-2-azabicyclo[2.2-2]oct-2-yl)-propyl]-2-methyl-1,3,4-oxadiazole;

5-[1,1-diphenyl-3-(exo-6-acetoxy-2-azabicyclo[2.2-2]oct-2-yl)-propyl]-2-methyl-1,3,4-oxadiazole;

5-[1,1-diphenyl-3-(exo-6-hydroxy-2-azabicyclo[2.2-2]oct-2-yl)-propyl]-2-methyl-1,3,4-oxadiazole;

1-(3,3,3-triphenylpropyl)-4-phenyl-4-piperidinecarboxylic acid hydrochloride;

ethyl 1-(3,3,3-triphenylpropyl)-4-phenyl-4-piperidinecarboxylate;

potassium 1-(3,3,3-triphenylpropyl)-4-phenyl-4-piperidinecarboxylate;

sodium 1-(3,3,3-triphenylpropyl)-4-phenyl-4-piperidinecarboxylate;

1-[3,3-diphenyl-3-(2-pyridyl)propyl]-4-phenyl-4-piperidinecarboxylic acid hydrochloride;

sodium 1-[3,3-diphenyl-3-(2-pyridyl)propyl]-4-phenyl-4-piperidinecarboxylate;
ethyl 1-[3,3-diphenyl-3-(2-pyridyl)propyl]-4-phenyl-4-piperidinecarboxylate;
potassium 1-[3,3-diphenyl-3-(2-pyridyl)propyl]-4-phenyl-4-piperidinecarboxylate;
1-(3,3,3-triphenylpropyl)-4-phenyl-4-piperidinemethanol;
1-[3,3-diphenyl-3-(2-pyridyl)propyl-4-phenyl-4-piperidinemethanol;
1-(3,3,3-triphenylpropyl)-4-phenyl-4-acetoxymethylpiperidine;
1-(3,3,3-triphenylpropyl)-4-phenyl-4-methoxymethylpiperidine;
1-(3,3,3-triphenylpropyl)-4-(4-chlorophenyl)-4-piperidinemethanol;
1-[3-(p-chlorophenyl)-3,3-diphenylpropyl]-4-(phenyl)-4-piperidinemethanol;
1-[3-(p-tolyl)-3,3-diphenylpropyl]-4-(phenyl)-4-piperidinemethanol;
1-[3-(p-bromophenyl)-3,3-diphenylpropyl]-4-(phenyl)-4-piperidinemethanol;
1-[3,3-diphenyl-3-(4-pyridyl)-propyl]-4-phenyl-4-piperidinemethanol;
1-[3,3-diphenyl-3-(3-pyridyl)propyl]-4-phenyl-4-piperidinemethanol;
1-(3,3,3-triphenylpropyl)-4-phenyl-4-hexoxymethylpiperidine;
1-(3,3,3-triphenylpropyl)-4-(p-tolyl)-4-piperidinemethanol;
1-(3,3,3-triphenylpropyl)-4-(p-trifluoromethyl)-4-piperidinemethanol;
1-(3,3,3-triphenylbutyl)-4-(phenyl)-4-piperidinemethanol;
1-(3,3,3-triphenylpropyl)-4-(phenyl)-4-piperidinemethanol;
1-(3,3,3-triphenylpropyl)-4-(phenyl)-4-methoxyethylpiperidine;
1-[3,3-diphenyl-3-(2-pyridyl)propyl]-4-phenyl-4-methoxyethylpiperidine;
1-(3,3,3-triphenylpropyl)-4-phenyl-4-piperidinemethanol;
1-[3,3-diphenyl-3-(2-pyridyl)propyl]-4-phenyl-4-piperidinemethanol;
1-(3,3,3-triphenylpropyl)-4-phenyl-4-acetoxymethylpiperidine;
1-(3,3,3-triphenylpropyl)-4-phenyl-4-methoxymethylpiperidine;
1-(3,3,3-triphenylpropyl)-4-(chlorophenyl)-4-piperidinemethanol;
1-(3,3,3-triphenylpropyl)-4-hydroxy-4-benzylpiperidine and 1-(3,3,3-triphenylpropyl)-4-hydroxy-4-benzylpiperidine; hydrochloride;
1-(3,3,3-triphenylpropyl)-4-hydroxy-4-p-chlorobenzylpiperidine;
1-(3,3,3-triphenylpropyl)-4-hydroxy-4-p-methylbenzylpiperidine;
1-[3,3,3(2-pyridyl)propyl]-4-benzyl-4-hydroxypiperidine;
m-chlomphenylamidinourea;
p-chlorophenylamidinourea;
3,4-dichlorophenylamidinourea;
m-bromophenylamidinourea;
p-bromophenylamidinourea;
3,4-dibromo-phenylamidinourea;
3-chloro-4-bromophenylamidinourea;
3-bromo-4-chlorophenylamidinourea;
3-chloro-4-fluorophenylamidinourea;
3-bromo-4-fluorophenylamidinourea;
3-fluoro-4-chlorophenylamidinourea;
2,6-dimethylphenylamidinourea;
2,6-diethylphenylamidinourea;
2-methyl-6-ethylphenylamidinourea;
2-methyl-6-methoxyphenylamidinourea;
2-methyl-6-ethoxyphenylamidinourea;
2-ethyl-6-methoxyphenylamidinourea;
2-ethyl-6-ethoxyphenylamidinourea;
3,4-dimethoxyphenylamidinourea;
3,4-dihydroxyphenylamidinourea;
3,4,5-trimethoxyphenylamidinourea;
3,4,5-trihydroxyphenylamidinourea;
2-[(2-methyl-3-aminophenyl)amino]-1-pyrroline, dihydrochloride;
2-[(2-methyl-3-acetamidophenyl)amino]-1-pyrroline, hydrochloride;
2-[(2-methyl-3-(ethoxycarbonylamino)phenyl-)amino]-1-pyrroline, hydrochloride;
2-(2,2-diphenylpentyl)-1-azabicylo[2.2.2]octane;
2-(2,2-diphenylhexyl)-1-azabicylo[2.2.2]octane;
2-(2,2-diphenylpropyl)-1-azabicylo[2.2.2]octane;
2-(2,2-diphenyloctyl)-1-azabicylo[2.2.2]octane; and
2-(2,2-diphenylheptyl)-1-azabicylo[2.2.2]octane.

Of these compounds, loperamide, [4-(p-chlorophenyl)-4-hydroxy-N-N-dimethyl-α,α-diphenyl-1-piperdenebutyramide monochloride]

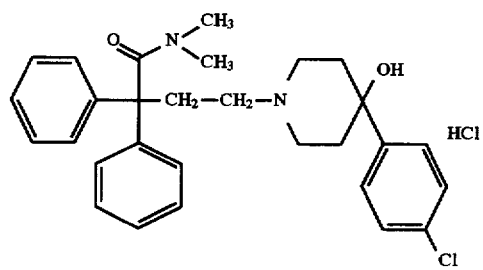

and the N-oxides of loperamide.

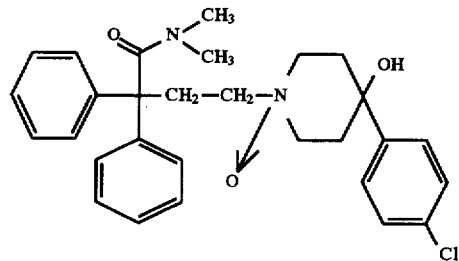

are most preferred.

The Film-Forming Polymers

The film-forming polymeric materials used in the present invention are described in U.S. Pat. No. 4,623,539 which is incorporated herein by reference. The film-forming materials are non-toxic, and contain no leachable components which would deleteriously affect the site of injury. The materials form a film or coating in the pH range of from about 5.5 to about 8.5 which adheres to the site of injury and delivers the anti-hyperalgesic compounds contained therein.

Broadly defined, the polymers capable of forming such films include certain anionic, cationic and neutral polymers.

I. Anionic Polymers

These polymers carry negative charges when in the ionized form. The anionic polymers bind to the cell surfaces and to protein molecules of the cells. The major forces responsible for these interactions are electrostatic in nature.

Suitable anionic polymers are represented by the generalized formulas:

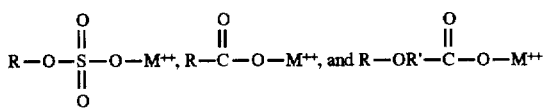

wherein R represents the polymeric chain or residue;

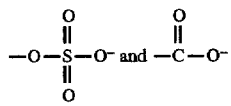

represent anionic ligands; and $M^{++}$ represents a divalent cation.

Specific anionic polymers useful in the present invention include:

A. sulfated polysaccharides;
B. carboxylated polysaccharides;
C. cellulose derivatives; and
D. sulfated, sulfonated or carboxylated synthetic polymers.

A. Sulfated Polysaccharides

Polysaccharides are polymeric carbohydrates which include sugars, cellulose, starch and glycogen. All the polysaccharides are glycosides in which the acetal carbon atoms of one monosaccharide unit is linked by way of an oxygen to one of the nonacetal carbon atoms of another monosaccharide, such as in:

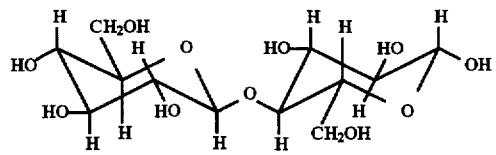

CELLOBIOSE (4-[β-glucosyl]-β-D-glucopyranose)

Sulfated sugar units in polysaccharides include 4-O-substituted D-galactopyranose and 2,6 disulphate residues, such as in carrageenan, which has the structural formula:

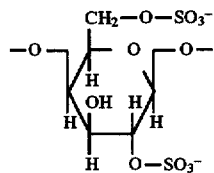

3-O-substituted N-acetyl-D-galactosamine; 4-sulfate residues as in chondroitin sulfate

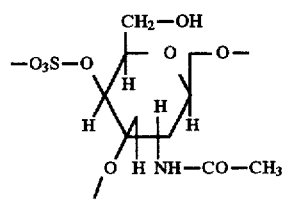

4-O substituted D-glucosamine residues as in heparin

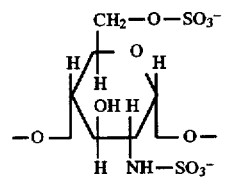

Sulfated esters of polysaccharides having the general formula:

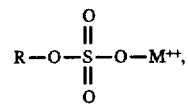

wherein, depending upon the specific polysaccharide, R consists of the following:

| Compound | R |
| --- | --- |
| kappa carrageenan | 3,6-anhydro-D-galactose linked through C-4 to D-galactose; |
| lambda carrageenan | α-D-galactose units (1→3) linked; |
| iota carrageenan | D-galactose 3,6-anhydro-D-galactose |
| Agar-Agar | D-galactose 3,6-anhydro-L-galactose |
| Furcellaren | D-galactose 3,6-anhydro-D-galactose |
| Laminaran sulfate | D-glucopyranose units linked through 1 and 3 positions by β-linkages; |
| Galactan sulfate | Galactan; and |
| Chondroitin sulfates | Galactosamino-glucuronans. |

The cation $M^{++}$ can be one of the following or a mixture of the following divalent metal ions: $Mg^{++}$, $Ca^{++}$, $Zn^{++}$, $Ba^{++}$.

B. Carboxylated Polysaccharides

Carboxylated polysaccharides am represented by the general formula

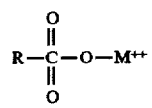

where R is as follows for various compounds:

| Compound | R |
| --- | --- |
| Pectin | D-galacturonoglycan in which the D-galactopyranosyluronic acid units are connected by (1→4) glycosidic linkages |
| Algin | anhydro-D-mannuronic acid and anhydro-L-guluronic acid residues |
| Gum karaya | complex polysaccharide, d-galacturonic acid, D-galactose, L-rhamnose |

The cation $M^{++}$ can be one of the following or a mixture of the following divalent metal ions: $Mg^{++}$, $Ca^{++}$, $Zn^{++}$, $Ba^{++}$.

C. Cellulose Derivatives

These polysaccharides are derivatives of the naturally occurring polysaccharide, cellulose. Representative compounds are salts of alkyl cellulose sulfate, salts of acyl cellulose sulfate, and salts of carboxyalkyl cellulose having the following formulas respectively:

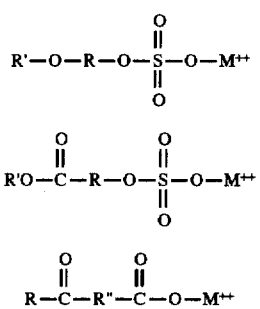

wherein:
R=anhydroglucose residue;
R'=$CH_3$; $C_2H_5$; $C_3H_7$;
R"=$CH_3$; $C_2H_5$; and
$M^{++}$=$Ca^{++}$, $Zn^{++}$, $Ba^{++}$, or $Mg^{++}$.
Specific examples of these compounds are:
Sodium ethylcellulose sulfate;
Sodium cellulose acetate sulfate; and
Sodium carboxymethyl cellulose.

D. Sulfated, Sulfonated or Carboxylated Synthetic Polymers

These polymers may have aliphatic or aromatic backbones with sulfonate, sulfate or carboxyl groups attached according to the following general formulas respectively:

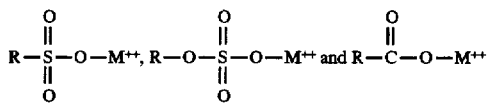

wherein R is an aliphatic or aromatic hydrocarbon chain such as polystyrene, poly(sulfone resin), or carboxylated (poly)vinyl, and $M^{++}$ is $Mg^{++}$, $Ca^{++}$, $Zn^{++}$, $Ba^{++}$.

II. Cationic Polymers

These polymers carry positive charges when in the ionized form. Aminopolysaccharides are representative of this group of polymers. These polymers are mainly of animal origin which contain units of amino sugars, most frequently D-glucosamine (2-amino-2-deoxy-D-galactose).

Representative compounds of this class have the general formula of:

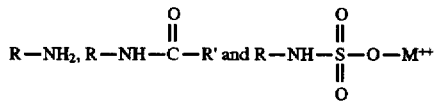

wherein R is a sugar residue, R' is $CH_3$ or $C_2H_5$, and $M^{++}$ is $Mg^{++}$, $Ca^{++}$, $Zn^{++}$, $Ba^{++}$.

Specific examples of such compounds are: Chondroitin Sulfates which can be characterized as being both anionic and cationic due to the electrostatic charges present, Dermatan Sulfate, Keratosulfate, Hyaluronic Acid, Heparin, and Chitin.

III. Neutral Polymers

Neutral polymers effective in the practice of the present invention are those which include atoms having polarizable electrons, such as oxygen, nitrogen, sulfur, fluoride, chloride, bromide and iodide. In the presence of a cation such as $Ca^{++}$, $Zn^{++}$, $Ba^{++}$ and $Mg^{++}$, these polymers are partially polarized, thus giving rise to the intermolecular interactions between the polymer and the protein molecules of the skin surface.

Representative polymers include:
A. Polysaccharides
Examples: Starch, Glycogen, Glucan, Fructans, Mannans, Galactomannans, Glucomannans, Galactans, Abrabinans, Xylans, Glycuranans, Guar Gum, Locust Bean Gum, Dextran, Starch Amylose, and Starch Amylopectin.
B. Cellulose Derivatives
Examples: Methylcellulose, Hydroxyethylcellulose, Ethylhydroxyethyl cellulose and Hydroxypropyl cellulose.
C. Synthetic Polymers
Examples: Polyvinylpyrrolidone, Polyvinyl alcohol, and Ethylene oxide polymers.

Formulations of the Present Invention

The formulations of the present invention comprise:
(a) of from about 1.0 to about 65% w/w of an anti-hyperalgesic compound;
(b) of from about 1 to about 76% w/w of a polymeric material having atoms containing polarizable electrons thereon in combination with a divalent cation in a ratio of from about 7.7 parts to about 1 part or less; and
(c) from about 23 to about 34% w/w of a pharmaceutically acceptable carrier.

The pharmaceutically acceptable carrier is an aqueous carrier in which both the anti-hyperalgesic compound and the polymeric material is at least partially water soluble; however compounds and materials which are essentially completely water soluble are preferred. To obtain sufficient solubility the aqueous carrier may contain solvents such as ethanol, t-butanol, hexane and glycol.

Formulations of the present invention can also be prepared in aerosol forms by nebulizing the formulations using a variety of nebulizing techniques known in the art, such as, forming a solution or a suspension of the polymer and the active agent contained therein in a liquid propellant. Both liquid and vapor phases are present in a pressurized container and when the valve of the container is opened, the liquid propellant containing the formulation is released producing and depositing a fine mist onto the site of treatment. The aerosol formulations typically contain of from about 30 to 80% w/w of a propellant, the remaining percentage being the active aqueous formulation. Propellants useful for practicing the invention include chlorinated, fluorinated and chlorofluorated lower molecular weight hydrocarbons, nitrous oxide, carbon dioxide, butane and propane.

Other ingredients, such as preservatives and dyes, may be included in the aqueous carrier of the film-forming composition comprising of from about 0.001 to about 1.5% of the aqueous carrier.

Ingredients which contribute to the healing of the site of injury by preventing infection and accelerating the healing process may also be used in the aqueous carrier of the film-forming composition comprising of from about 0.001 to about 5.0% w/w of the aqueous carrier. Such ingredients are well known to those skilled in the art of healing and include antibacterials, antivirals, antifungals, anti-inflammatories, anesthetics and mixtures thereof. These ingredients are described by the various editions of the Physicians Desk Reference (such as PDR, 1993 Edition) and are incorporated herein by reference. Non-limiting, illustrative examples are:

Antibacterial agents, such as Streptomycin, Rifamycin, Ampicillin, Penicillin O, Penicillin V, Bacitracin, Doxycycline, Methacycline, Minocycline, Tetracycline, Acetyl Sulfisoxazole, Succinylsulfathiazole, Sulfaloxic Acid, Sulfapyrazine, and Acetosulfone.

Antifungal agents, such as Dermostatin, Fungichromin, Clotrimazole, Econazole, Potassium Iodide and Propionic Acid.

Anti-inflammatory agents, such as Diclofenac, Tolmetin, Ibuprofen, Protizinic Acid, Glycol Salicylate and Sulfasalazine.

13

Antiseptic Agents, such as Chlorhexidine, Calcium Iodate, Iodine, Chloroxylenol, Hexachlorophene, Boric Acid, and Cuptic Sulfate.

Antiviral agents, such as Acyclovir, Trifluridine and Zidovudine.

The following formulation examples illustrate, without limitation, the present invention.

EXAMPLE 1

The formulation is prepared by mixing the ingredients together until the mixture is homogeneous. The pH is adjusted to about 7.0.

|  | Weight % |
|---|---|
| Loperamide HCl | 25.0 |
| Sodium Carrageenan | 25.0 |
| Calcium Lactate | 32.0 |
| Q.S. with water to | 100.0 |

EXAMPLE 2

The formulation is prepared by dissolving loperamide HCl in ethanol followed by mixing the other ingredients until the mixture is homogeneous. The pH is adjusted to about 8.0.

|  | Weight % |
|---|---|
| Loperamide HCl | 30.0 |
| Ethanol | 20.0 |
| Sodium Ethylcellulose Sulfate | 25.0 |
| Calcium Lactate | 10.0 |
| Q.S. with water to | 100.0 |

EXAMPLE 3

The procedure used in Example 2 was followed. The pH is adjusted to about 5.5.

|  | Weight % |
|---|---|
| 4-(p-chlorophenyl)-4-hydroxy-N-N-dimethyl-α,α-diphenyl-1-piperidenebutyramide, N-oxide | 50.0 |
| Ethanol | 10.0 |
| Pectin-NF | 10.0 |
| Calcium Lactate | 5.0 |
| Q.S. with water to | 100.0 |

EXAMPLE 4

The procedure of Example 2 was followed. The pH is adjusted to about 8.5.

|  | Weight % |
|---|---|
| Loperamide HCl | 15.0 |
| Benzyl Alcohol | 10.0 |
| Polyvinylpyrrolidone | 30.0 |
| Zinc Chloride | 20.0 |
| Q.S. with water to | 100.0 |

EXAMPLE 5

The procedure of Example 2 was followed. The pH is adjusted to about 6.5.

|  | Weight % |
|---|---|
| Loperamide HCl | 60.0 |
| Starch Amylose | 15.0 |
| Ethanol | 5.0 |
| Calcium Lactate | 10.0 |
| Q.S. with water to | 100.0 |

In preparing the formulations of the present invention the film-forming materials are dissolved in water and the viscosity of the solution is measured using a Brookfield viscometer. Typical viscosities for various film-forming materials are shown in Table I.

TABLE I

| Solution | Viscosity in cps |
|---|---|
| 1% Gelcarin-HMR | 200 |
| 3.5% Gelcarin-HMR | 22,000 |
| 6.5% Gelcarin-HMR | 86,000 |
| 1% Gelcarin-DG | 16,000 |
| 2% Gelcarin-DG | 60,000 |
| 2.5% Gelcarin-DG | 86,000 |
| 3% Gelcarin-DG | 141,000 |
| 4% Gelcarin-DG | 230,500 |
| 1% Gelcarin-DG + 1% Ca lactate | 5,000 |
| 3.5% Gelcarin-DG + 3.5% Ca lactate | 48,000 |
| 3.5% Viscarin | 41,000 |
| 3.5% Viscarin Ba$^{++}$ | 38,000 |
| 3.5% Viscarin 3.5% Ca lactate | 42,000 |
| 4% Viscarin | 80,000 |
| 3.5% Viscarin-DG + 3.5% Ca lactate | 76,000 |
| 1% Klucel | 1,200 |
| 2% Klucel | 20,000 |
| 2% Pectin | 280 |
| 3% Pectin | 1,150 |
| 3.5% Pectin | 1,800 |
| 4% Pectin | 4,100 |
| 5% Pectin | 13,500 |
| 3.5% Polystyrene sulfonic acid | 250 |
| 3.5% Starch H-50B | 1,700 |
| 3.5% Starch 36,46:5 | 1,500 |
| 3.5% Chondroitin Sulfate "C" | 50 |

The required amount of the anti-hyperalgesic compound is dissolved in an organic solvent, such as ethanol, and added to the solution of the film-forming material. Other ingredients, such as preservatives, antibacterials, disinfectants and the like, are then added directly to the solution or, alternatively, may be first dissolved in a suitable solvent prior to their addition to the solution.

The desired viscosities of a formulation may be adjusted by the further addition of solvents, other ingredients such as viscosity increasing and buffering agents and/or water. In so doing, the desired consistency of the formulation can be obtained in the form of a solution, suspension, lotion, paste and cream. These techniques are well-known to those skilled in the art.

In the method of treatment, a formulation is applied to the site of the inflamed/injured area by depositing the same thereon in the form of a solution, suspension, lotion, cream, paste or spray-on aerosol and allowing the formulation to form a coating. The active ingredients are then in intimate contact with the site of application, are bioavailable to the underlining skin surface, and effect reduction/elimination of pain without causing CNS side effects.

It should be understood by those skilled in the art that, while the invention has been described and illustrated above in connection with certain specific embodiments, many variations and modifications may be employed without departing from the scope of the invention.

What is claimed is:

1. A topical anti-hyperalgesic film-forming composition for coating an injured/inflamed site on the mammalian patient to reduce hyperalgesia of said injured/inflamed site comprising:

a) of from about 1 to about 65% w/w of an anti-hyperalgesic compound selected from the group consisting of 2-[4-(4-hydroxy-4-phenylpiperidino)-2,2-diphenylbutyryl]-piperidine;
4-{4-[4-hydroxy-4-(3-trifluoromethylphenyl)piperidinol]-2,2-diphenylbutyryl}morpholine;
1-{4-[4-hydroxy-4-(3-trifluoromethylphenyl)piperidino]-2,2-diphenylbutyl}piperidine;
4-(p-chlorophenyl)-4-hydroxy-N-N-,y-trimethyl-α,α-diphenylpiperidine-1-butyramide;
4-(p-chlorophenyl)-4-hydroxy-N-N-dimethyl-α,α-diphenylpiperidine-1-butyramide[loperamide];
4-(3,4-dichlorophenyl)-N-N-diethyl-4-hydroxy-α,α-diphenylpiperidine-1-butyramide;
4-(3,4-dichlorophenyl)-4-hydroxy-N-N-dimethyl-α,α-diphenylpiperidine-1-butyramide
4-(chloro-3-trifluoromethylphenyl)-4-hydroxy-N-N-dimethyl-α,α-diphenylpiperidine-1-butyramide;
4-(p-fluorophenyl)-4-hydroxy-N-N-,y-trimethyl-α,α-diphenylpiperidine-1-butyramide;
4-(p-bromophenyl)-4-hydroxy-N-N-dimethyl-α,α-diphenylpiperidine-1-butyramide;
1-{4-[4-(3,4-dichlorophenyl)-4-hydroxypiperidine]-2,2-diphenylbutyl}pyrrolidine;
4-(p-chlorophenyl)-N-ethyl-4-hydroxy-N-methyl-α,α-diphenylpiperidine-1-butyramide;
5-[1,1-diphenyl-3-(exo-5-hydroxy-2-azabicyclo[2,2-2]oct-2-yl)-propyl]-2-methyl-1,3,4-oxadiazole;
5-[1,1-diphenyl-3-(exo-5-acetoxy-2-azabicyclo[2,2-2]oct-2-yl)-propyl]-2-methyl-1,3,4-oxadiazole;
5-[1,1-diphenyl-3-(endo-5-acetoxy-2-azabicyclo[2,2-2]oct-2-yl)-propyl]-2-methyl-1,3,4-oxadiazole;
5-[1,1-diphenyl-3-(endo-5-hydroxy-2-azabicyclo[2,2-2]oct-2-yl)-propyl]-2-methyl-1,3,4-oxadiazole;
5-[1,1-diphenyl-3-(endo-6-acetoxy-2-azabicyclo[2,2-2]oct-2-yl)-propyl]-2-methyl-1,3,4-oxadiazole;
5-[1,1-diphenyl-3-(endo-6-hydroxy-2-azabicyclo[2,2-2]oct-2-yl)-propyl]-2-methyl-1,3,4-oxadiazole;
5-[1,1-diphenyl-3-(exo-6-acetoxy-2-azabicyclo[2,2-2]oct-2-yl)-propyl]-2-methyl-1,3,4-oxadiazole;
5-[1,1-diphenyl-3-(exo-6-hydroxy-2-azabicyclo[2,2-2]oct-2-yl)-propyl]-2-methyl-1,3,4-oxadiazole;
1-(3,3,3-triphenylpropyl)-4-phenyl-4-piperidinecarboxylic acid hydrochloride;
ethyl 1-(3,3,3-triphenylpropyl)-4-phenyl-4-piperidinecarboxylate;
potassium 1-(3,3,3-triphenylpropyl)-4-phenyl-4-piperidinecarboxylate;
sodium 1-(3,3,3-triphenylpropyl)-4-phenyl-4-piperidinecarboxylate;
1-[3,3-diphenyl-3-(2-pyridyl)propyl]-4-phenyl-4-piperidinecarboxylic acid hydrochloride;
sodium 1-[3,3-diphenyl-3-(2-pyridyl)propyl]-4-phenyl-4-piperidinecarboxylate;
ethyl 1-[3,3-diphenyl-3-(2-pyridyl)propyl]-4-phenyl-4-piperidinecarboxylate;
potassium 1-[3,3-diphenyl-3-(2-pyridyl)propyl]-4-phenyl-4-piperidinecarboxylate;
1-(3,3,3-triphenylpropyl)-4-phenyl-4-piperidinemethanol;
1-[3,3-diphenyl-3-(2-pyridyl)propyl-4-phenyl-4-piperidinemethanol;
1-(3,3,3-triphenylpropyl)-4-phenyl-4-acetoxymethyl-piperidine;
1-(3,3,3-triphenylpropyl)-4-phenyl-4-methoxymethyl-piperidine;
1-(3,3,3-triphenylpropyl)-4-(4-chlorophenyl)-4-piperidinemethanol;
1-[3-(p-chloropheny)-3,3-diphenylpropyl]-4-(phenyl)-4-piperidinemethanol;
1-[3-(p-tolyl)-3,3-diphenylpropyl]-4-(phenyl)-4-piperidinemethanol;
1-[3-(p-bromophenyl)-3,3-diphenylpropyl]-4-(phenyl)-4-piperidinemethanol;
1-[3,3-diphenyl-3-(4-pyridyl)-propyl]-4-phenyl-4-piperidinemethanol;
1-[3,3-diphenyl-3-(3-pyridyl)propyl]-4-phenyl-4-piperidinemethanol;
1-(3,3,3-triphenylpropyl)-4-phenyl-4-hexoxymethyl-piperidine;
1-(3,3,3-triphenylpropyl)-4-(p-tolyl)-4-piperidinemethanol;
1-(3,3,3-triphenylpropyl)-4-(p-trifluoromethyl)-4-piperidinemethanol;
1-(3,3,3-triphenylbutyl)-4-(phenyl)-4-piperidinemethanol;
1-(3,3,3-triphenylpropyl)-4-(phenyl)-4-piperidinemethanol;
1-(3,3,3-triphenylpropyl)-4-(phenyl)-4-methoxyethylpiperidine;
1-[3,3-diphenyl-3-(2-pyridyl)propyl]-4-phenyl-4-methoxyethylpiperidine;
1-(3,3,3-triphenylpropyl)-4-phenyl-4-piperidinemethanol;
1-[3,3-diphenyl-3-(2-pyridyl)propyl]-4-phenyl-4-piperidinemethanol;
1-(3,3,3-triphenylpropyl)-4-phenyl-4-acetoxymethylpiperidine;
1-(3,3,3-triphenylpropyl)-4-phenyl-4-methoxymethylpiperidine;
1-(3,3,3-triphenylpropyl)-4-(chlorophenyl)-4-piperidinemethanol;
1-(3,3,3-triphenylpropyl)-4-hydroxy-4-benzylpiperidine and 1-(3,3,3-triphenylpropyl)-4-hydroxy-4-benzylpiperidine;
hydrochloride;
1-(3,3,3-triphenylpropyl)-4-hydroxy-4-p-chlorobenzylpiperidine;
1-(3,3,3-triphenylpropyl)-4-hydroxy-4-p-methylbenzylpiperidine;
1-[3,3,3-(2-pyridyl)propyl]-4-benzyl-4-hydroxypiperidine;
m-chlorophenylamidinourea;
p-chlorophenylamidinourea;
3,4-dichlorophenylamidinourea;
m-bromophenylamidinourea;
p-bromophenylamidinourea;
3,4-dibromo-phenylamidinourea;
3-chloro-4-bromophenylamidinourea;
3-bromo-4-chlorophenylamidinourea;
3-chloro-4-fluorophenylamidinourea;
3-bromo-4-fluorophenylamidinourea;
3-fluoro-4-chlorophenylamidinourea;
2,6-dimethylphenylamidinourea;
2,6-diethylphenylamidinourea;
2-methyl-6-ethylphenylamidinourea;
2-methyl-6-methoxyphenylamidinourea;
2-methyl-6-ethoxyphenylamidinourea;
2-ethyl-6-methoxyphenylamidinourea;

2-ethyl-6-ethoxyphenylamidinourea;
3,4-dimethoxyphenylamidinourea;
3,4-dihydroxyphenylamidinourea;
3,4,5-trimethoxyphenylamidinourea;
3,4,5-trihydroxyphenylamidinourea;
2-[(2-methyl-3-aminophenyl)amino]-1-pyrroline, dihydrochloride;
2-[(2-methyl-3-acetamidophenyl)amino]-1-pyrroline, hydrochloride;
2-[(2-methyl-3-(ethoxycarbonylamino)phenyl-)amino]-1-pyrroline, hydrochloride;
2-(2,2-diphenylpentyl)-1-azabicylo[2,2,2]octane;
2-(2,2-diphenylhexyl)-1-azabicylo[2,2,2]octane;
2-(2,2-diphenylpropyl)-1-azabicylo[2,2,2]octane;
2-(2,2-diphenyloctyl)-1-azabicylo[2,2,2]octane; and
2-(2,2-diphenylheptyl)-1-azabicylo[2,2,2]octane, said anti-hyperalgesic compound incorporated in a film-forming material, said anti-hyperalgesic compound being devoid of central nervous system side effects when topically delivered to the mammalian patient;

b) said film-forming polymeric material being present in said composition of from about 1 to about 76% w/w and is capable of forming an essentially continuous film in the pH environment of about 5.5 to 8.5, said polymeric material having atoms contain polarizable electrons thereon, said atoms being selected from the group consisting of oxygen, nitrogen, sulfur, in combination with a divalent cation, said divalent cation selected from the group consisting of $CA^{++}$, $MG^{++}$, $Zn^{++}$ and $Ba^{++}$, wherein the ratio of said atoms containing the polarizable electrons to said divalent catons is in the range of from about 7.7 to about 1, said film-forming material selected from the group consisting of sodium ethylcellulose sulfate,
sodium cellulose acetate sulfate,
sodium carboxyethyl cellulose,
chondroitin sulfate,
dermatan sulfate,
keratosulfate,
lyaluronic acid,
heparin,
chitin,
polyinyl pyrrolidone,
polyvinyl alcohol,
polyethylene oxide; and c) of from about 23 to about 34% w/w of an aqueous pharmaceutically acceptable carrier.

2. The topical anti-hyperalgesic film-forming composition of claim 1 further comprising a pharmacologically active agent selected from the group consisting of an antibacterial, antiviral, antifungal, anti-inflammatory and anesthetic agents, said agent constituting about 0.001 to about 5.0% w/w of said aqueous pharmaceutically acceptable carrier.

3. A method of treating peripheral hyperalgesia comprising topically administering to a mammal in need of such treatment an effective amount of the topical anti-hyperalgesic film-forming composition of claim 1.

4. The method of claim 3 wherein said compound is selected from the group consisting of:

2-[4-(4-hydroxy-4-phenylpiperidino)-2,2-diphenylbutyryl]-piperidine;
4-{4-[4-hydroxy-4-(3-trifluoromethylphenyl)piperidino]-2,2-diphenylbutyryl}morpholine;
1-{4-[4-hydroxy-4-(3-trifluoromethylphenyl)-piperidino]-2,2-diphenylbutyl}piperidine;
4-(p-chlorophenyl)-4-hydroxy-N-N-,y-trimethyl-α,α-diphenylpiperidine-1-butyramide;
4-(p-chlorophenyl)-4-hydroxy-N-N-dimethyl-α,α-diphenylpiperidine-1-butyramide[loperamide];
4-(3,4-dichlorophenyl)-N-N-diethyl-4-hydroxy-α,α-diphenylpiperidine-1-butyramide;
4-(3,4-dichlorophenyl)-4-hydroxy-N-N-dimethyl-α,α-diphenylpiperidine-1-butyramide
4-(4-chloro-3-trifluoromethylphenyl)-4-hydroxy-N-N-dimethyl-α,α-diphenylpiperidine-1-butyramide;
4-(p-fluorophenyl)-4-hydroxy-N-N-,y-trimethyl-α,α-diphenylpiperidine-1-butyramide;
4-(p-bromophenyl)-4-hydroxy-N-N-dimethyl-α,α-diphenylpiperidine-1-butyramide;
1-{4-[4-(3,4-dichlorophenyl)-4-hydroxypiperidine]-2,2-diphenylbutyryl}pyrrolidine;
4-(p-chlorophenyl)-N-ethyl-4-hydroxy-N-methyl-α,α-diphenylpiperidine-1-butyramide;
5-[1,1-diphenyl-3-(exo-5-hydroxy-2-azabicyclo[2,2-2]oct-2-yl)-propyl]-2-methyl-1,3,4-oxadiazole;
5-[1,1-diphenyl-3-(exo-5-acetoxy-2-azabicyclo[2,2-2]oct-2-yl)-propyl]-2-methyl-1,3,4-oxadiazole;
5-[1,1-diphenyl-3-(endo-5-acetoxy-2-azabicyclo[2,2-2]oct-2-yl)-propyl]-2-methyl-1,3,4
5-oxadiazole;
5-[1,1-diphenyl-3-(endo-5-hydroxy-2-azabicyclo[2,2-2]oct-2-yl)-propyl]-2-methyl-1,3,4-oxadiazole;
5-[1,1-diphenyl-3-(endo-6-acetoxy-2-azabicyclo[2,2-2]oct-2-yl)-propyl]-2-methyl-1,3,4-oxadiazole;
5-[1,1-diphenyl-3-(endo-6-hydroxy-2-azabicyclo[2,2-2]oct-2-yl)-propyl]-2-methyl-1,3,4-oxadiazole;
5-[1,1-diphenyl-3-(exo-6-acetoxy-2-azabicyclo[2,2-2]oct-2-yl)-propyl]-2-methyl-1,3,4-oxadiazole;
5-[1,1-diphenyl-3-(exo-6-hydroxy-2-azabicyclo[2,2-2]oct-2-yl)-propyl]-2-methyl-1,3,4-oxadiazole;
1-(3,3,3-triphenylpropyl)-4-phenyl-4-piperidinecarboxylic acid hydrochloride;
ethyl 1-(3,3,3-triphenylpropyl)-4-phenyl-4-piperidinecarboxylate;
potassium 1-(3,3,3-triphenylpropyl)-4-phenyl-4-piperidinecarboxylate;
sodium 1-(3,3,3-triphenylpropyl)-4-phenyl-4-piperidinecarboxylate;
1-[3,3-diphenyl-3-(2-pyridyl)propyl]-4-phenyl-4-piperidinecarboxylic acid hydrochloride;
sodium 1-[3,3-diphenyl-3-(2-pyridyl)propyl]-4-phenyl-4-piperidinecarboxylate;
ethyl 1-[3,3-diphenyl-3-(2-pyridyl)propyl]-4-phenyl-4-piperidinecarboxylate;
potassium 1-[3,3-diphenyl-3-(2-pyridyl)propyl]-4-phenyl-4-piperidinecarboxylate;
1-(3,3,3-triphenylpropyl)-4-phenyl-4-piperidinemethanol;
1-[3,3-diphenyl-3-(2-pyridyl)propyl-4-phenyl-4-piperidinemethanol;
1-(3,3,3-triphenylpropyl)-4-phenyl-4-acetoxymethyl-piperidine;
1-(3,3,3-triphenylpropyl)-4-phenyl-4-methoxymethyl-piperidine;
1-(3,3,3-triphenylpropyl)-4-(4-chlorophenyl)-4-piperidinemethanol;

1-[3-(p-chlorophenyl)-3,3-diphenylpropyl]-4-(phenyl)-4-piperidinemethanol;

1-[3-(p-tolyl)-3,3-diphenylpropyl]-4-(phenyl)-4-piperidinemethanol;

1-[3-(p-bromophenyl)-3,3-diphenylpropyl]-4-(phenyl)-4-piperidinemethanol;

1-[3,3-diphenyl-3-(4-pyridyl)-propyl]-4-phenyl-4-piperidinemethanol;

1-[3,3-diphenyl-3-(3-pyridyl)propyl]-4-phenyl-4-piperidinemethanol;

1-(3,3,3-triphenylpropyl)-4-phenyl-4-hexoxymethylpiperidine;

1-(3,3,3-triphenylpropyl)-4-(p-tolyl)-4-piperidinemethanol;

1-(3,3,3-triphenylpropyl)-4-(p-trifluoromethyl)-4-piperidinemethanol;

1-(3,3,3-triphenylbutyl)-4-(phenyl)-4-piperidinemethanol;

1-(3,3,3-triphenylpropyl)-4-(phenyl)-4-piperidinemethanol;

1-(3,3,3-triphenylpropyl)-4-(phenyl)-4-methoxyethylpiperidine;

1-[3,3-diphenyl-3-(2-pyridyl)propyl]-4-phenyl-4-methoxyethylpiperidine;

1-(3,3,3-triphenylpropyl)-4-phenyl-4-piperidinemethanol;

1-[3,3-diphenyl-3-(2-pyridyl)propyl]-4-phenyl-4-piperidinemethanol;

1-(3,3,3-triphenylpropyl)-4-phenyl-4-acetoxymethylpiperidine;

1-(3,3,3-triphenylpropyl)-4-phenyl-4-methoxymethylpiperidine;

1-(3,3,3-triphenylpropyl)-4-(chlorophenyl)-4-piperidinemethanol;

1-(3,3,3-triphenylpropyl)-4-hydroxy-4-benzylpiperidine and 1-(3,3,3-triphenylpropyl)-4-hydroxy-4-benzylpiperidine; hydrochloride;

1-(3,3,3-triphenylpropyl)-4-hydroxy-4-p-chlorobenzylpiperidine;

1-(3,3,3-triphenylpropyl)-4-hydroxy-4-p-methylbenzylpiperidine;

1-[3,3,3(2-pyridyl)propyl]-4-benzyl-4-hydroxypiperidine;

m-chlomphenylamidinourea;
p-chlorophenylamidinourea;
3,4-dichlorophenylamidinourea;
m-bromophenylamidinourea;
p-bromophenylamidinourea;
3,4-dibromo-phenylamidinourea;
3-chloro-4-bromophenylamidinourea;
3-bromo-4-chlorophenylamidinourea;
3-chloro-4-fluorophenylamidinourea;
3-bromo-4-fluorophenylamidinourea;
3-fluoro-4-chlorophenylamidinourea;
2,6-dimethylphenylamidinourea;
2,6-diethylphenylamidinourea;
2-methyl-6-ethylphenylamidinourea;
2-methyl-6-methoxyphenylamidinourea;
2-methyl-6-ethoxyphenylamidinourea;
2-ethyl-6-methoxyphenylamidinourea;
2-ethyl-6-ethoxyphenylamidinourea;
3,4-dimethoxyphenylamidinourea;
3,4-dihydroxyphenylamidinourea;
3,4,5-trimethoxyphenylamidinourea;
3,4,5-trihydroxyphenylamidinourea;
2-[(2-methyl-3-aminophenyl)amino]-1-pyrroline, dihydrochloride;
2-[(2-methyl-3-acetamidophenyl)amino]-1-pyrroline, hydrochloride;
2-[(2-methyl-3-(ethoxycarbonylamino)phenyl-)amino]-1-pyrroline, hydrochloride;
2-(2,2-diphenylpentyl)-1-azabicylo[2.2.2]octane;
2-(2,2-diphenylhexyl)-1-azabicylo[2.2.2]octane;
2-(2,2-diphenylpropyl)-1-azabicylo[2.2.2]octane;
2-(2,2-diphenyloctyl)-1-azabicylo[2.2.2]octane; and
2-(2,2-diphenylheptyl)-1-azabicylo[2.2.2]octane.

5. The method of claim 3 wherein said composition further comprising a pharmacologically active agent selected from the group consisting of an antibacterial, antiviral, antifungal, anti-inflammatory and anesthetic agents said agent constituting about 0.001 to about 5.0% w/w of said aqueous pharmaceutically acceptable carrier.

* * * * *